United States Patent
Müller et al.

(10) Patent No.: US 7,226,406 B2
(45) Date of Patent: Jun. 5, 2007

(54) AT LEAST PARTIALLY IMPLANTABLE HEARING SYSTEM

(75) Inventors: Gerd M Müller, Lohhof (DE); Hans Leysieffer, Taufkirchen (DE)

(73) Assignee: Cochlear Limited, Lane Cove, NSW (AU)

( * ) Notice: Subject to any disclaimer, the term of this patent is extended or adjusted under 35 U.S.C. 154(b) by 0 days.

(21) Appl. No.: 09/938,533

(22) Filed: Aug. 27, 2001

(65) Prior Publication Data

US 2002/0038072 A1  Mar. 28, 2002

(30) Foreign Application Priority Data

Sep. 25, 2000 (DE) ................... 100 47 388

(51) Int. Cl.
*H04R 25/00* (2006.01)
(52) U.S. Cl. ...................................................... 600/25
(58) Field of Classification Search .................. 600/25, 600/559; 606/60, 130; 607/55, 56, 57; 623/10, 623/11.11, 16.11; 381/312
See application file for complete search history.

(56) References Cited

U.S. PATENT DOCUMENTS

| | | |
|---|---|---|
| 3,712,962 A | 1/1973 | Epley |
| 3,870,832 A | 3/1975 | Fredrickson |
| 3,882,285 A | 5/1975 | Nunley et al. |
| 4,850,962 A | 7/1989 | Schaefer |
| 5,015,224 A | 5/1991 | Maniglia |
| 5,015,225 A | 5/1991 | Hough et al. |
| 5,277,694 A | 1/1994 | Leysieffer et al. |
| 5,279,292 A | 1/1994 | Baumann et al. |
| 5,554,096 A | 9/1996 | Ball |
| 5,624,376 A | 4/1997 | Ball et al. |
| 5,707,338 A | 1/1998 | Adams et al. |
| 5,788,711 A | 8/1998 | Lehner et al. |
| 5,814,095 A | 9/1998 | Müller et al. |
| 5,935,170 A * | 8/1999 | H.ang.kansson et al. ...... 606/73 |
| 5,941,814 A | 8/1999 | Lehner et al. |
| 5,999,632 A | 12/1999 | Leysieffer et al. |
| 6,077,215 A | 6/2000 | Leysieffer |
| 6,123,660 A | 9/2000 | Leysieffer |
| 6,162,169 A | 12/2000 | Leysieffer |
| 6,293,903 B1 * | 9/2001 | Kasic et al. ................... 600/25 |
| 6,325,755 B1 * | 12/2001 | Bushek et al. ................ 600/25 |
| 6,517,476 B1 * | 2/2003 | Bedoya et al. ................ 600/25 |

FOREIGN PATENT DOCUMENTS

WO        WO 98/06235        2/1998

(Continued)

OTHER PUBLICATIONS

Leysieffer et al., "Ein implantierbarer piezoelektrischer Hörerätewandler für Innenohrschwerhörige", pp. 792-800, Oct. 1997, HNO.

(Continued)

*Primary Examiner*—Max F. Hindenburg
*Assistant Examiner*—Jonathan Foreman
(74) *Attorney, Agent, or Firm*—Jagtiani + Guttag

(57) ABSTRACT

An at least partially implantable hearing system comprising at least one electromechanical output transducer; a micromanipulator for positioning the transducer and for fixing the transducer in a position set by the micromanipulator, the micromanipulator being adapted to be fixedly attached by fixing means to a skull cap; and a releasable coupling unit disposed between the transducer and the micromanipulator, said coupling unit, in an assembled state, fixing the transducer with respect to the micromanipulator, and, in a released state, permitting removal of the transducer from the micromanipulator.

12 Claims, 6 Drawing Sheets

FOREIGN PATENT DOCUMENTS

| | | |
|---|---|---|
| WO | WO 98/06236 | 2/1998 |
| WO | WO 98/06237 | 2/1998 |
| WO | WO 98/06238 | 2/1998 |
| WO | WO 00/48426 | 8/2000 |

OTHER PUBLICATIONS

Zenner et al., "Aktive elekronische Hörimplante für Mittel-und Innenohrschwerhörige- eine neue Ära der Ohrchirurgie", pp. 749-774, Oct. 1997, HNO.

Leysieffer et al., Ein vollständig implantierbares Hörsystem für Innenohrschwerhörige: TICA LZ 3001, pp. 853-863 and 844-852, 1998, HNO.

Suzuki et al., Implantation of Partially Implantable Middle Ear Implant and the Indication, pp. 160-166, 1988, Adv. Audiol., vol. 4.

Yanagihara et al., "Efficacy of the Partially Implantable Middle Ear Implant in Middle and Inner Ear Disorders", pp. 149-159, 1988, Adv. Audiol., vol. 4.

Maniglia et al., Contactless Semi-implantable Electromagnetic Middle Ear, pp. 121-141, Feb. 1995, Otolaryngologic Clinics of North America, vol. 28, No. 1.

Fredrickson et al., "Ongoing Inestigations into an Implantable Electromagnetic Hearing Aid for Moderate to Serve Sensorineural Hearling Loss", pp. 107-121, Feb. 1995, Otolaryngologic Clinics of North America, vol. 28, No. 1.

* cited by examiner

AT LEAST PARTIALLY IMPLANTABLE HEARING SYSTEM

BACKGROUND OF THE INVENTION

1. Field of the Invention

This invention relates to an at least partially implantable hearing system comprising at least one electromechanical output transducer and a micromanipulator for positioning the transducer and for fixing the transducer in a position set by the micromanipulator, the micromanipulator being adapted to be fixedly attached by fixing means to a cranial vault.

2. Description of Related Art

The expression "at least partially implantable hearing system" is defined here as a system in which a sound signal is picked up by at least one sensor which transduces a sound signal into an electrical signal (microphone function), in which this electrical signal is electronically further processed and amplified, and in which an output signal of the system causes an electromechanical stimulation of the damaged hearing, wherein at least one component of the system, particularly the electromechanical output transducer, is designed for being implanted.

The expression "hearing dsefder disorder" is defined here as including any type of inner ear and middle ear damage, any combined inner ear and middle ear damage, and a temporary or permanent noise impression (tinnitus).

Hearing systems of the presently considered type usually comprise at least one acoustic sensor (microphone) for picking up acoustic signals and converting them into electrical audio sensor signals, an electronic signal processing unit for audio signal processing and amplification, an electrical power supply unit which supplies individual components of the system with energy, and an electromechanically actoric output arrangement including at least one electromechanical transducer for stimulation of the middle and/or inner ear. This transducer is connected to a mechanical positioning and fixing system which here is termed "micromanipulator" and which is fixedly and permanently attached to the cranial vault. In the case of a fully implantable hearing system in which the implant is provided with a secondary storage element for electrical energy, the system further comprises a wireless transcutaneoiis charging device.

Electronic measures for rehabilitation of inner ear damage which cannot be cured by surgery have currently achieved great importance. With total failure of the inner ear, cochlear implants with direct electrical stimulation of the remaining auditory nerves are in routine clinical use. For medium to severe inner ear damage, for the first time, fully digital hearing devices are presently being used which open up a new world of electronic audio signal processing and offer expanded possibilities of controlled audiological fine tuning of the hearing devices to the individual inner ear damage. In spite of major improvements of hearing aid hardware achieved in recent years, in conventional hearing aids, there remain basic defects which are caused by the principle of acoustic amplification, i.e. especially by the reconversion of the electronically amplified signals into airborne sound. These defects include aspects such as the visibility of the hearing aids, poor sound quality as a result of electromagnetic transducers (speakers), closed external auditory canal as well as feedback effects at high acoustic gain.

As a result of these fundamental defects, there has long been the desire to move away from conventional hearing aids with acoustic stimulation of the damaged inner ear and to replace them by partially or fully implantable hearing systems with direct mechanical stimulation. Implantable hearing systems differ from conventional hearing aids: the acoustic signal is converted with a proper microphone into an electrical signal and amplified in an electronic signal processing stage; this amplified electrical signal, however, is not sent to an electroacoustical transducer (speaker), but rather to an implanted electromechanical transducer providing for output-side mechanical vibrations which are sent directly, and therefore with direct mechanical contact, to the middle ear or inner ear, or indirectly via an air gap in, for example, electromagnetic converter systems. This principle applies regardless of whether implantation of all necessary system elements is partial or complete and also regardless of whether an individual with pure inner ear impairment with a completely intact middle ear or an individual with combined hearing impairment, in which the middle and inner ear is damaged, is to be rehabilitated. Therefore implantable electromechanical transducers and methods for coupling the mechanical transducer vibrations to the functioning middle ear or directly to the inner ear for rehabilitation of a pure inner ear impairment, or to a remaining ossicle of the middle ear in the case of an artificially or pathologically altered middle ear for taking care of a hearing disorder caused by a disturbance of sound conduction, or for combinations of such disorders, have been described in the recent scientific literature and in many patents.

Useful electromechanical transducer processes include basically all physical transducer principles, such as electromagnetic, electrodynamic, magnetostrictive, dielectric and piezoelectric. Various research groups, in recent years, have focused essentially on two of these processes, namely electromagnetic and piezoelectric processes. A survey can be found in H. P. ZENNER and H. LEYSIEFFER (HNO 10/1997, vol. 45, pp. 749–774).

In the piezoelectric process, direct mechanical coupling of the output-side transducer vibrations to the middle ear ossicle or to the oval window is essential. In the electromagnetic principle, force coupling between the transducer and ossicle, on the one hand, can take place "without contact", i.e. via an air gap; in this case, only the permanent magnet is caused to vibrate by the transducer being in direct mechanical contact with the middle ear ossicle by permanent fixation. On the other hand, it is possible to implement the transducer entirely in a housing (in this case the coil and the magnet preferably being coupled with the smallest possible air gap) and to transmit the output-side vibrations via a mechanically stiff coupling element with direct contact to the middle ear ossicle (see FREDRICKSON et al.: *Ongoing investigations into an implantable electromagnetic hearing aid for moderate to severe sensorineural hearing loss;* Otolaryngologic Clinics of North America, Vol. 28/1 (1995), pp. 107–121; and H. Leysieffer et al., HNO 10/97, vol. 45, pp. 792–800).

The patent literature contains some of the aforementioned versions of both electromagnetic and also piezoelectric hearing aid transducers: U.S. Pat. No. 3,712,962, EPLEY; U.S. Pat. No. 3,870,832, FREDRICKSON; U.S. Pat. No. 3,882,285, NUNLEY et al.; U.S. Pat. No. 4,850,962, SCHAEFER; U.S. Pat. No. 5,015,224, MANIGLIA; U.S. Pat. No. 5,277,694, LEYSIEFFER et al.; U.S. Pat. No. 5,554,096, BALL; U.S. Pat. No. 5,707,338, ADAMS et al.; U.S. Pat. No. 6,123,660, LEYSIEFFER; U.S. Pat. No. 6,162,169, LEYSIEFFER; International Patent Application Publications WO-A 98/06235, ADAMS et al.; WO-A 98/06238, ADAMS et al.; WO-A 98/06236, KROLL et al.; WO-A 98/06237, BUSHEK et al.

The partially implantable piezoelectric hearing system of the Japanese group of Suzuki and Yanigahara presupposes, for implantation of the transducer, the absence of the middle ear ossicles and a free tympanic cavity to be able to couple the piezo element to the stapes (Yanigahara et al.: *Efficacy of the partially implantable middle ear implant in middle and inner ear disorders:* Adv. Audiol., Vol. 4, Karger Basel (1988), pp. 149–159; Suzuki et al.: *Implantation of partially implantable middle ear implant and the indication.* Adv. Audiol., Vol. 4, Karger Basel (1988), pp. 160–166). Likewise, in the method of implanting a hearing system for inner ear hearing-impaired according to SCHAEFER (U.S. Pat. No. 4,850,962) basically the incus is removed in order to be able to couple a piezoelectric transducer element to the stapes. This also applies to further developments which are based on the SCHAEFER technology and which are described in the above mentioned patents (U.S. Pat. No. 5,707,338, ADAMS et al.; International Patent Application Publications WO-A 98/06235, ADAMS et al.; WO-A 98/06238, ADAMS et al.; WO-A 98/06236, KROLL et al.; WO-A 98/06237, BUSHEK et al.).

The BALL electromagnetic transducer ("Floating Mass Transducer FMT" of U.S. Pat. No. 5,554,096, BALL; U.S. Pat. No. 5,624,376, BALL et al.) is, on the other hand, directly fixed to the long process of the incus when the middle ear is intact. The electromagnetic transducer of the partially implantable system of FREDRICKSON (Fredrickson et al.: *Ongoing investigations into an implantable electromagnetic hearing aid for moderate to severe sensorineural hearing loss*, Otolaryngologic Clinics of North America, Vol. 28/1 (1995), pp. 107–121) is directly mechanically coupled to the body of the body of the incus when the ossicular chain of the middle ear is likewise intact. The same applies to the piezoelectric transducers of LEYSIEFFER (LEYSIEFFER et al.: *An implantable piezoelectric hearing aid converter for the inner ear hearing-impaired.* HNO 1997/45, pp. 792–800; U.S. Pat. No. 5,277,694, LEYSIEFFER et al.; U.S. Pat. No. 6,123,660, LEYSIEFFER; U.S. Pat. No. 6,162,169, LEYSIEFFER). Also in the electromagnetic transducer system of MANIGLIA (MANIGLIA et al.: *Contactless semi-implantable electromagnetic middle ear device for the treatment of sensorineural hearing loss,* Otolaryngologic Clinics of North America, Vol. 28/1 (1995), pp. 121–141) with the ossicular chain intact a permanent magnet is permanently mechanically fixed to the ossicular chain, but is mechanically driven via an air gap coupling by a coil.

In the described transducer and coupling versions, basically, two implantation principles can be distinguished:
a) In the case of the one principle the electromechanical transducer with its active transducer element is located itself in the middle ear region in the tympanic cavity and the transducer is directly connected there to an ossicle or to the inner ear (U.S. Pat. Nos. 4,850,962, 5,015,225, 5,707,338, 5,624,376, 5,554,096, and International Patent Application publication Nos. WO 98/06235, WO 98/06238, WO 98/06236, and WO 98/06237).
b) In the other principle the electromagnetic transducer with its active transducer element is located outside of the middle ear region in an artificially formed mastoid cavity; the output-side mechanical vibrations are then transmitted to the middle or inner ear by means of mechanically passive coupling elements via suitable surgical accesses (the natural aditus ad antrum (U.S. Pat. No. 6,077,215), opening of the chorda-facialis angle or via an artificial hole from the mastoid (Fredrickson et al.: *Ongoing investigations into an implantable electromagnetic hearing aid for moderate to severe sensorineural hearing loss.* Otolaryngologic Clinics of North America, Vol. 28/1 (1995), pp. 107–121; U.S. Pat. No. 5,277,694; U.S. Pat. No. 6,123,660; U.S. Pat. No. 6,162,169). This type of access requires an implantable positioning and fixing system (micromanipulator) for "suspending" the electromagnetic transducer, wherein the positioning and fixing system is to be fixedly and durably attached to the skull (U.S. Pat. No. 5,788,711 and commonly owned U.S. patent application Ser. No. 09/468,853).

An advantage of the a) type versions is, that the transducer can be made as a so-called "floating mass" transducer, i.e., the transducer element does not require any "reaction" via secure screwing to the skull bone, but it vibrates based on the laws of mass inertia with its transducer housing and transmits these vibrations directly to a middle ear ossicle (U.S. Pat. Nos. 5,624,376, 5,554,096, and 5,707,338, and International Patent Application publication no. WO 98/06236). On the one hand, this means that an implantable fixation system on the cranial vault can be advantageously omitted; on the other hand, this version disadvantageously means that bulky artificial elements must be placed in the tympanic cavity, and their long-term stability and biostability are currently not known or guaranteed, especially in the case of temporary pathological changes of the middle ear (for example, otitis media). Another major disadvantage is that the transducer together with its electrical supply line has to be transferred from the mastoid into the middle ear and must be fixed there using suitable surgical tools; this requires an expanded access through the chorda facialis angle, and thus, entails a latent hazard to the facial nerve which is located in the immediate vicinity. Furthermore, such "floating mass" transducers can be used merely in a very limited manner or not at all, when the inner ear is to be directly stimulated for example via the oval window, or when, due to pathological changes, for example the incus is substantially damaged or is no longer present, so that such a transducer no longer can be mechanically connected to an ossicle that is able to vibrate and is in connection with the inner ear.

A certain disadvantage of the transducer versions as per b) is that the transducer housing is to be attached to the cranial vault with the aid of implantable positioning and fixation systems (micromanipulators) (advantageous embodiment U.S. Pat. No. 5,788,711). A further disadvantage of the transducer versions as per b) is that a recess is to be made, preferably by an appropriate laser, in the respective ossicle in order to allow the application of the coupling element. This, on the one hand, is technically complicated and expensive and, on the other hand, involves risks for the patient. Both in the partially implantable system of FREDRICKSON (*"Ongoing investigations into an implantable electromagnetic hearing aid for moderate to severe sensorineural hearing loss"*, Otolaryngologic Clinics of North America, Vol. 28/1 (1995), pp. 107–121) as well as in the fully implantable hearing system of LEYSIEFFER and ZENNER (HNO 1998, vol. 46, 853–863 and 844–852), when the vibrating transducer part is coupled to the body of the incus, it is assumed that for permanent and mechanically secure vibration transmission the tip of the coupling rod which is placed in the laser-induced depression of the middle ear ossicle undergoes osseointegration over the long term, i.e., the coupling rod coalesces solidly with the ossicle and thus ensures reliable transmission of dynamic compressive and tensile forces. However, this long-term effect is currently not yet scientifically proven or certain. Furthermore, in this type of coupling, in case of a technical transducer defect, there is the disadvantage that decoupling from the ossicle to remove the transducer can only be done with mechanically based surgical methods; this can mean considerable hazard to the middle ear and especially the inner ear. Therefore further coupling elements, partly involving novel surgical access paths, were developed which minimize or no longer have the above mentioned disadvantages (U.S. Pat. No. 5,941,814, LEHNER et al., commonly owned U.S. patent applications Ser. Nos. 09/576,009; 09/613,560; 09/626,745; 09/680,489).

The major advantages of these converter embodiments as per b), however, are that the middle ear remains largely free, and that access to the middle and inner ear can take place in a manner which permits, when using a properly designed micromanipulator, reaching of basically any point of the middle ear or of the inner ear, respectively, as stimulation site. One preferable surgical process for this purpose is described in U.S. Pat. No. 6,077,215, LEYSIEFFER. This results in the further advantage that basically all combinations of middle and inner ear damages can be attended, and that a pure inner ear stimulation likewise is possible via a direct access, for example an artificial window, and by using proper coupling elements. In this connection a detachable interconnection between transducer and coupling element has been disclosed in commonly owned U.S. patent application Ser. No. 09/680,489.

In a hearing system known from International Patent Application Publication WO 00/48426 a unit consisting of an actoric electromechanical transducer and of a positioning and fixation system (here called "micromanipulator") is detachably connected to mounting means fixedly attached to the skull, so that in case of need the micromanipulator together with the transducer may be exchanged without disassembly of the mounting means being required. In fact, the removal of the mounting means may require a relatively invasive intervention because the operative access to the fixing screws of the micromanipulator must be exposed. Furthermore it my happen that the respective screw holes in the cranial vault can not be reused because the screws normally are self-cutting and the respective holes in the bone are widened during unscrewing and no longer can provide for an absolutely secure seat of new screws. It may also happen that the "old" access path to the point of aim of the transducer coupling element can be used no longer or only in a very restricted manner. However, the prior solution still leaves much to be desired. Thus, after an exchange of the micromanipulator/transducer unit this unit must be newly adjusted in a troublesome manner in order to exactly align the transducer with the aimed site of stimulation. Thereby the reversion operation becomes distinctly more risky and prolonged, particularly when the transducer postoperatively became defect and therefore an exchange of the transducer is required. In addition it may happen that the intervention, which otherwise possibly could take place under local anesthesia, must be carried out under total anesthesia because the depth and duration of the operation make this necessary. The fixed interconnection between transducer and micromanipulator furthermore involves the technical drawback that it becomes extremely difficult to find a design for both components which avoids left-hand/right-hand differences of the system. This leads to the economical disadvantage that for each new implantation two complete transducer-micromanipulator systems must be delivered because it may be that only shortly before the operation the decision is made together with the patient which side will be operated. Another economical disadvantage is that a reversion operation because of a defect of the transducer requires explantation and throwing away of a fully functioning micromanipulator because the existing laws prohibit a reuse thereof. An other important drawback is that, with the further developments of the electromechanical transducers to be expected, such improved products again can be offered to a patient already wearing an implant merely in the form of a complete exchange of a system involving both the transducer and the micromanipulator.

SUMMARY OF THE INVENTION

A primary object of the present invention is to devise an at least partially implantable hearing system which simplifies the measures which become required in case of a defect of the electromechanical output transducer, and which system, if desired, also may be retrofitted with an improved transducer in a relatively simple manner.

This object is achieved by an at least partially implantable hearing system comprising at least one electromechanical output transducer; a micromanipulator for positioning the transducer and for fixing the transducer in a position set by the micromanipulator, the micromanipulator being adapted to be fixedly attached by fixing means to the cranial vault; and a releasable coupling unit disposed between the transducer and the micromanipulator, said coupling unit, in an assembled state, fixing the transducer with respect to the micromanipulator, and, in a released state, permitting removal of the transducer from the micromanipulator.

On occurrence of a postoperative transducer defect the releasable coupling unit provided for in conformity with the invention permits an exchange of the transducer alone, that is without exchanging the micromanipulator, too. The same is true when an exchange of the transducer becomes desirable for other reasons, for example when improved transducers become available due to further developments of the transducer technology. The transducer position adjusted by the micromanipulator is preserved even in case of an exchange of the transducer, so that a new adjustment of the micromanipulator does not become necessary. In view of the fact that the transducer alone may be exchanged, the above discussed problems with respect to left-hand/right-hand differences also do not occur.

Furthermore, in conformity with the invention, the releasable coupling preferably comprises a transducer-side coupling element and a micromanipulator-side coupling element, which coupling elements are adapted to be selectively mechanically engaged with each other and disengaged from each other, respectively, wherein the transducer-side coupling element may be designed for being fixedly connected, for example adhesively connected, to the transducer already during production of the transducer, or for being fixedly connected to the transducer, for example by a permanent snap-in connection, in the course of the implantation of the transducer.

The micromanipulator-side coupling element may define means for receiving the transducer-side coupling element.

Within the scope of the invention at least one of the coupling elements may be at least partially made of elastic material, particularly of a soft polymer, preferably silicone, polytetrafluoroethylene or polyurethane. Thereby a feedback of body sound from the transducer to the skull can be prevented or at least reduced. However, dependent on the design of the coupling, also both coupling elements may be made of a hard polymer, such as a hard polymeric material, a biocompatible metal or a ceramic material.

The releasable coupling unit may be designed as a snap-in coupling, wherein, for example, the micromanipulator-side coupling element is a rigid annular receiver member, whilst the transducer-side coupling element is at least partially elastic and is adapted to snap into the rigid annular receiver member in a substantially axial direction. In conformity with a modified embodiment of a snap-in coupling the micromanipulator-side coupling element comprises an expandable fork, and the transducer-side coupling element is adapted to be snapped into this fork in a substantially radial direction.

Furthermore, the micromanipulator-side coupling element may comprise an expandable receiver member, whilst the transducer-side coupling element is adapted to be inserted into this receiver member in a substantially axial direction and is adapted to be locked in a position in which the transducer-side coupling element is detained.

In conformity with a further embodiment of the invention, the micromanipulator-side coupling element may comprise a pair of expandable tongs, and the transducer-side coupling element may be adapted to be introduced between the tongs in a substantially axial direction, wherein preferably locking means, for example a sleeve which is mounted for sliding movement along a portion of the tongs, are provided for locking the expandable tongs in a closed position in which the transducer-side coupling element is detained.

According to a further embodiment of the invention the releasable coupling unit may comprises a plug-type coupling including a pair of coupling elements one of which is adapted to be inserted into the other one, wherein these coupling elements, in the assembled state of the coupling, are held engaged with each other by an interference fit. In this embodiment one coupling element may include a dovetailed portion, and the other coupling element may include a complementary receiving groove adapted to receive the dovetailed portion.

Preferably, the micromanipulator, the transducer and the coupling elements are designed in a manner avoiding any left-hand/right-hand differences, i.e. such that the same combination of micromanipulator and transducer may be used for the right-hand ear as well as for the left-hand ear. For this purpose at least one of the two coupling elements may be rotationally symmetrical and/or the micromanipulator-side coupling element may be axially symmetrical with respect to an axis of the transducer.

Any desired transducer principle may be used within the scope of the invention. Particularly, the electromechanical output transducer may be selected from the group consisting of electromagnetic, electrodynamic, magnetostrictive, dielectric and piezoelectric transducers and of combinations of such transducers.

The described system can be designed to be monaural or binaural, and the coupling may be designed for being selectively engaged and disengaged manually or with the aid of a suitable tool These and further objects, features and advantages of the present invention will become apparent from the following description when taken in connection with the accompanying drawings which, for purposes of illustration only, shows several embodiments in accordance with the present invention.

DETAILED DESCRIPTION OF THE INVENTION

Figure 1:
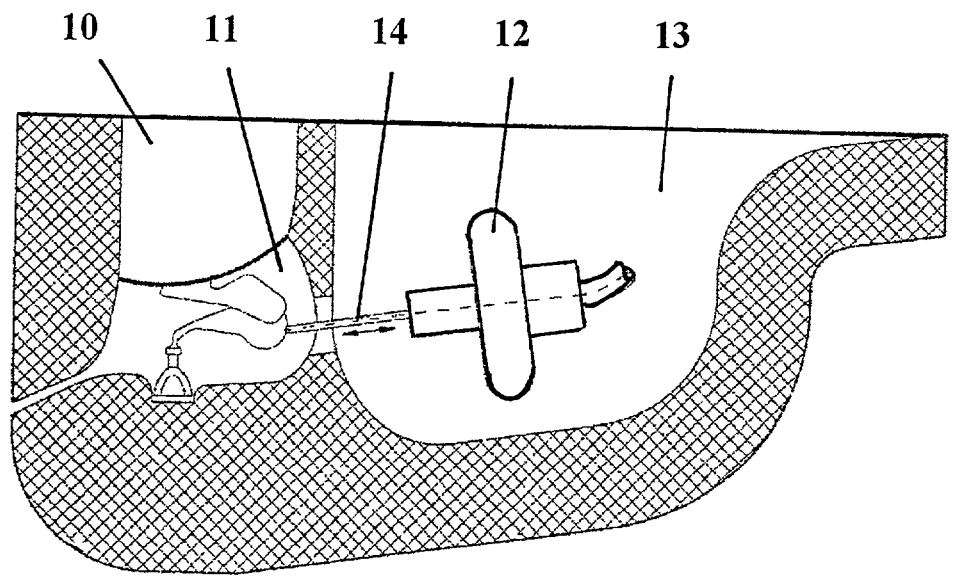
FIG. 1 shows a schematic sectional view of a human petrous bone with a transducer being disposed in a mastoid cavity.

FIG. 1 shows a schematic sectional view of a human petrous bone including the external auditory canal 10, the middle ear 11 comprising the auditory ossicles malleus, incus and stapes (with the inner ear not being illustrated), and an electromechanical transducer 12 which is disposed in an artificial mastoid cavity 13. The transducer 12, in a manner known per se, is induced to mechanical vibrations, and in this embodiment the transducer 12 transmits such vibrations to the incus via a coupling rod 14 which extends through the natural access aditus ad antrum. The implantable positioning and fixing system (micromanipulator) is not illustrated in FIG. 1.

Figure 2:
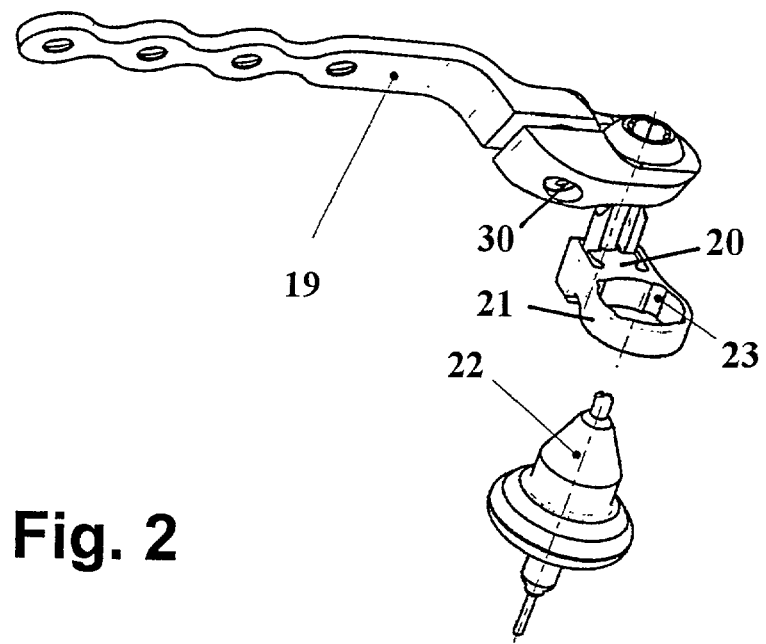
FIG. 2 shows an embodiment of an implantable micromanipulator and of an associated transducer.

FIG. 2 shows an embodiment of an implantable micromanipulator 18 of the type described in detail in commonly owned U.S. patent application Ser. No. 09/468,853 which is hereby incorporated by reference. The micromanipulator 18 comprises an osteosynthesis plate 19 which is adapted to be fixed by screws to the cranial vault. Micromanipulator 18 further includes a transducer carriage 20 which is provided with a micromanipulator-side coupling element 21. The coupling element 21 defines a receiver 23 for the transducer 12. In this embodiment, receiver 23 is in the form of a closed ring. A transducer-side coupling element 22 is connected to the transducer 12 and, together with the micromanipulator-side coupling element 21 defines a releasable coupling. Transducer 12 connected to coupling element 22 is adapted to be inserted and releasably fixed in the receiver 23.

Figure 3:
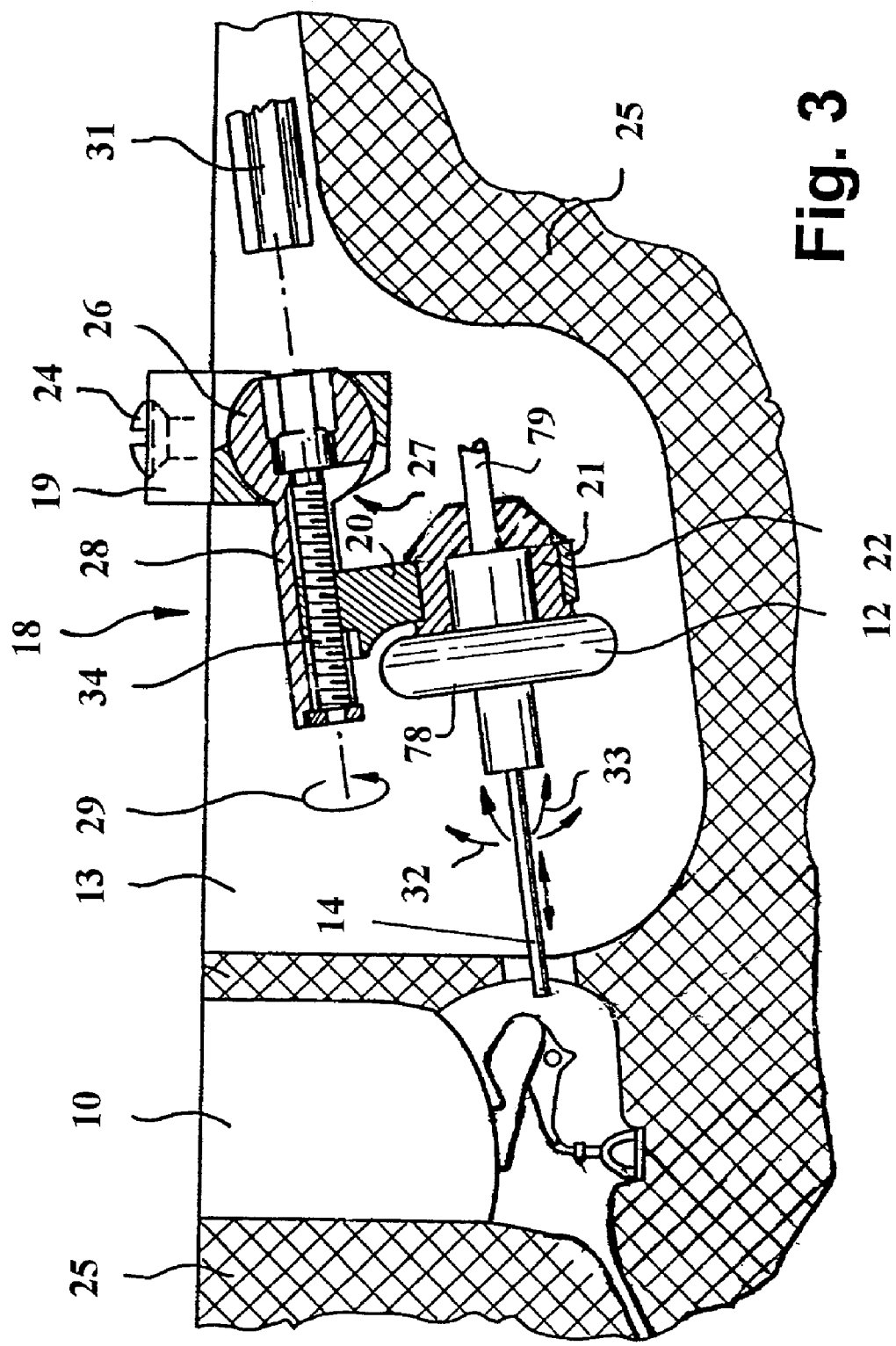
FIG. 3 shows the arrangement of the micromanipulator together with the transducer within the mastoid cavity.

FIG. 3 shows details of the micromanipulator 18 and of the arrangement thereof, together with the electromechanical transducer 12 releasably attached thereto, in the implanted state within the mastoid cavity 13. The osteosynthesis plate 19 is securely screwed onto the cranial vault 25 by means of bone screws 24. The osteosynthesis plate 19 is rotatably (arrow 29) and pivotally connected to a straight guide rail 28 via a ball-and-socket joint 27 having a ball 26. The ball-and-socket joint 27 is adapted to be locked by tightening a clamping screw 30 (FIG. 2). Upon loosening of the clamping screw 30, ball 26 can be freely swivelled within its socket by a tool 31 in all three rotational degrees of freedom indicated by arrows 29, 32 and 33. A threaded spindle 34 is mounted on the member consisting of ball 26 and guide rail 28 so that it can be freely rotated, but is prevented from movement in axial direction. An external thread of threaded spindle 34 is in threaded engagement with an internal thread of a spindle nut which is part of the transducer carriage 20. The carriage 20, together with transducer 12 disposed in receiver 23, can be moved axially along the guide rail 28 by rotating the threaded spindle 34 by means of a tool (not shown). In the illustrated embodiment the longitudinal axis of transducer 12 and coupling rod 14 extends at least approximately parallel to the longitudinal axes of threaded spindle 34 and of guide rail 28, but is laterally offset with respect to the longitudinal axis of threaded spindle 34.

Figure 4:
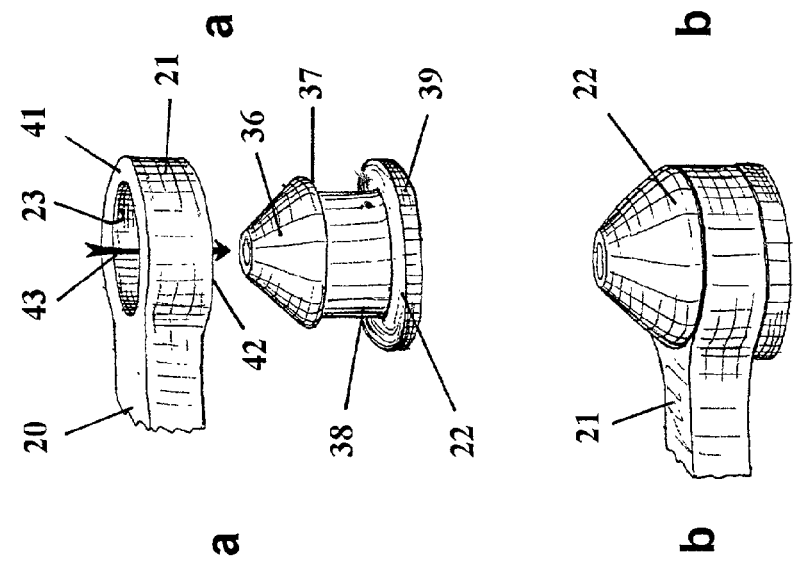
FIG. 4a and 4b show an embodiment of a releasable snap-in coup ling between micromanipulator and transducer.

FIGS. 4*a* and 4*b* show an embodiment of a releasable snap-in-locking type coupling between micromanipulator 18 and transducer 12. The transducer-side coupling element 22 of this coupling is defined by an elastic snout and includes a truncated head 36 having a base 37, a circular cylindrical neck 38 and a collar 39, which follow each other in axial direction. The base 37 of head 36 has a diameter which is slightly larger than the diameter of neck 38. Collar 39 radially projects from neck 38 at the side of neck 38 remote from head 36. The receiver 23 defined by the micromanipulator-side coupling element 21 is circular cylindrical and has an inner diameter which is about the same as the outer diameter of neck 38 but is smaller than the diameters of base 37 and of collar 39. The axial dimension of neck 38 of the transducer-side coupling element 22 is at least approximately equal to the axial dimension of the transducer receiver 23 of micromanipulator 18.

The elastic transducer-side coupling element 22 is adapted to be axially pushed into the receiver 23 of the micromanipulator-side coupling element 21, wherein head 36 is slightly deformed. As soon as the truncated head base 37 of coupling element head 36 again exits the receiver 23 (in FIGS. 4*a* and 4*b* in upward direction), the coupling element 22 snaps into the receiver 23 and is securely mechanically locked therein, with the receiver 23 enclosing the neck 38 and the mutually facing sides of head 36 and collar 39 abutting the sides 41 and 42, respectively, of carriage 20 in the region of receiver 23 (FIG. 4*b*). When the transducer 12 is to be detached from the micromanipulator 18, the head 36 of coupling element 22 may be slightly compressed by hand or with the aid of a proper tool, and the coupling element 22 may be extracted from the carriage 20 as indicated in FIG. 4*a* by arrow 43.

Further embodiments are illustrated in FIGS. 5 to 9, wherein again the released state is shown in section a and the assembled state is shown in section b.

Figure 5:
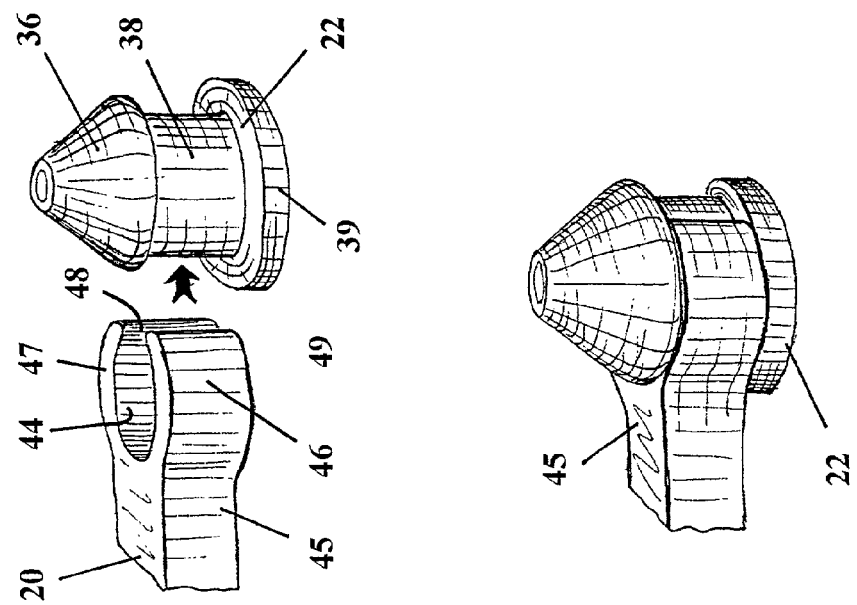
FIGS. 5a and 5b show a further embodiment of a releasable snap-in coupling between micromanipulator and transducer.

FIG. 5 shows a further embodiment of a releasable snap-in-locking type coupling between micromanipulator 18 and transducer 12 of FIG. 1. In this case the carriage 20 comprises a micromanipulator-side coupling element 45 which is fork-shaped and which defines a receiver 44 for the coupling element 22 connected to transducer 12. The receiver 44 is radially open at one side thereof The free ends of fork arms 46, 47 having essentially the same length delimit a fork opening 48 the width of which is smaller by a predetermined amount than the outer diameter of neck 38 of the transducer-side coupling element 22. The fork arms 46, 47 may be rigid, if the coupling element 22 is elastic at least within the neck region thereof However, the coupling element 22 also may be rigid, if the coupling element 45 is somewhat elastic. Furthermore both the fork 45 and the transducer-side coupling element 22 may be elastically resilient. In any case, the coupling element 22, which in a manner not shown in more detail is connected to transducer 12, may be snapped into the receiver 44 and locked therein by being moved in a direction which is radial to the axis of the coupling element. A movement of the coupling element 22 in the opposite direction (arrow 49) permits detaching the coupling element 22 from the receiver 44.

Figure 6:
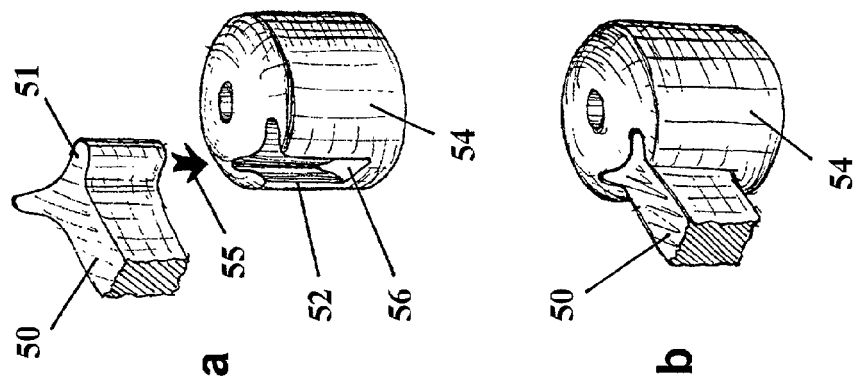
FIGS. 6a and 6b show an embodiment of a releasable plug-type coupling between micromanipulator and transducer.

FIG. 6 shows an embodiment of a releasable plug-type coupling between the micromanipulator 18 and the transducer 12 of FIG. 1. In this case the carriage 20, different from the illustration in FIGS. 2 and 3, comprises a micromanipulator-side coupling element 50 which is widened in a dovetailed manner at its free end 51 and which is adapted to be slid (arrow 55) into a complementary receiving groove 52 of a coupling element 54 connected to the transducer 12 (not shown in FIG. 6). Receiving groove 52 is open at one end thereof (the upper end in FIG. 6). An end wall 56 of receiving groove 52, which is opposite to the open end of the groove, defines a stop for the coupling element 50. In this embodiment both the transducer-side coupling element 54 and the micromanipulator-side coupling element 50 may be mechanically rigid. In this case the interconnection between transducer and micromanipulator is effected by a combined form-locking and frictional locking engagement. However, it is also possible that at least one of the elements 50, 54 is elastic at least within the respective coupling region.

Figure 7:
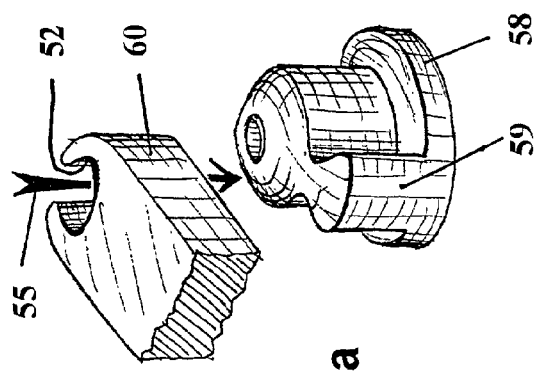
FIGS. 7a and 7b show a further embodiment of a releasable plug-type coupling between micromanipulator and transducer.
Figure 7:
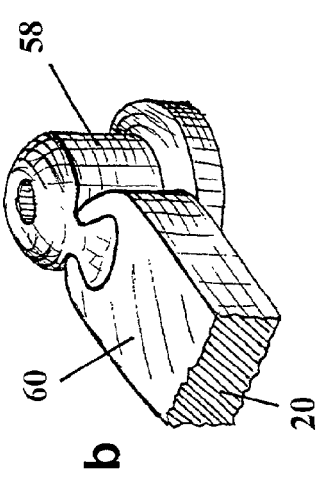

In the embodiment of FIG. 7 a transducer-side coupling element 58 has a dovetailed portion 59, and the complementary receiving groove 52 is provided in a micromanipulator-side coupling element 60 of the transducer carriage 20. Apart from this reversal of the dovetailed portion and the complementary receiving groove, the embodiment of FIG. 7 corresponds to that of FIG. 6.

Figure 8:
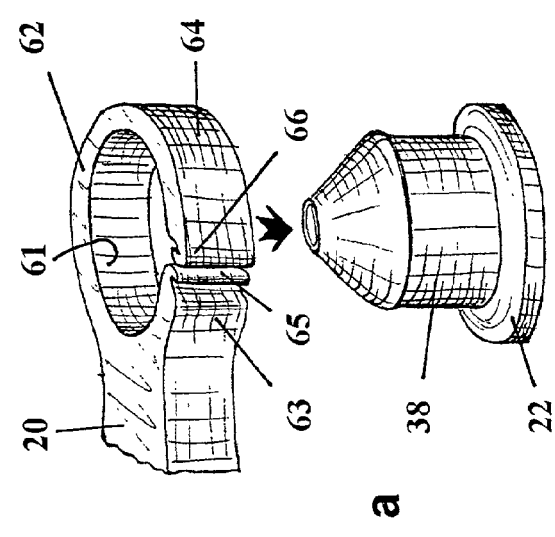
FIGS. 8a and 8b show an embodiment of a releasable coupling between micromanipulator and transducer comprising a micromanipulator-side coupling element which defines an expandable receiver member.
Figure 8:
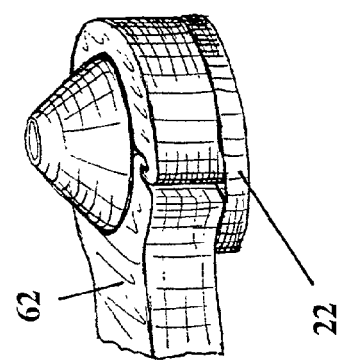

In the embodiment of FIG. 8 the releasable coupling between micromanipulator 18 and transducer 12 of FIG. 1 comprises a micromanipulator-side coupling element 62 defining an annular receiver 61 which may be expanded and which is adapted to be locked in a closed position. The micromanipulator-side coupling element 62 includes a shorter leg 63 and a longer leg 64. The legs 63, 64 are provided with complementary hook-shaped ends 65 and 66, respectively. The hooks 65, 66 may be mutually disengaged for expanding the receiver 61 and for detaching the transducer 12 from the micromanipulator 18 (FIG. 8*a*). The hooks 65, 66 at first also are disposed in this position when the transducer 12 is to be connected to the micromanipulator 18. After the neck 38 of the transducer-side coupling element 22 has been introduced into the receiver 61, pressure is applied to the longer leg 64 such that the hooks 65, 66 are engaged with each other (FIG. 8*b*). In this embodiment the transducer-side coupling element 22 may be mechanically rigid or elastic. At least the longer leg 64 of the micromanipulator-side coupling element 62 has spring characteristics.

Figure 9:
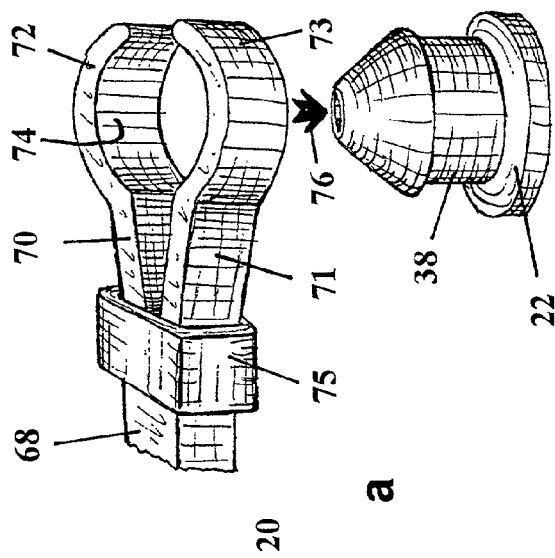
FIGS. 9a and 9b show an embodiment of a releasable coupling between micromanipulator and transducer comprising a micromanipulator-side coupling element in form of expandable tongs which are adapted for being locked in a closed position.
Figure 9:
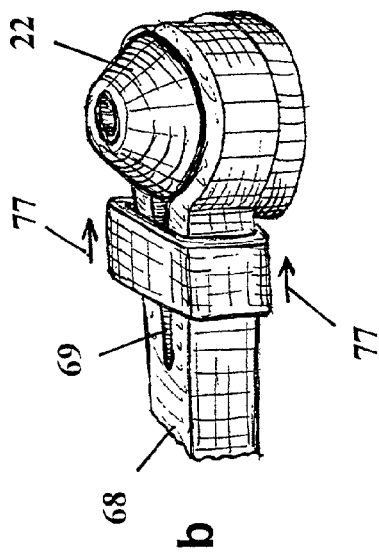

FIG. 9 shows a further embodiment of the releasable coupling between micromanipulator 18 and transducer 12. In this embodiment the micromanipulator-side coupling element 68 of the carriage 20 comprises a pair of expandable tongs which are obtained in that a longitudinal slot 69 separates the portion of carriage 20 remote from the spindle 34 into two elastic arms 70, 71. In the closed state of the tongs, free ends 72, 73 of the arms 70, 71 define an annular receiver 74 for the transducer-side coupling element 22. The slot 69 extends from the receiver 74 towards the guide rail 28 of the micromanipulator 18. The arms 70, 71 are spring-biased into an expanded position (FIG. 9*a*) in which their free ends 72, 73 are disposed so as to permit the transducer-side coupling element 22 to be inserted into the receiver 74 and to be released from the receiver 74, respectively (arrow 76 in FIG. 9a). A slideable sleeve 75 extends around the coupling element 68. Sleeve 75 can be slideable moved along coupling element 68 between a position in which the arms 70, 71 are released for expansion (FIG. 9a) and a position closer to the free ends 72, 73 (arrows 77 in FIG. 9b). In the latter position sleeve 75 urges the arms 70, 71 towards each other against the spring biasing force until the ends 72, 73 enclose the neck 38 of the transducer-side coupling element 22 to thereby securely hold the transducer-side coupling element together with the transducer 12 (not shown) connected thereto (FIG. 9b). In this embodiment the transducer-side coupling element 22 may be mechanically rigid or elastic.

In all of the embodiments described above the transducer 12 and the transducer-side coupling element 22 or 54 or 58, respectively, may be fixedly interconnected, for example mechanically locked or securely adhesively connected to each other. An integral interconnection of transducer and transducer-side coupling element is also possible. A further alternative consists in securely connecting the transducer-side coupling element to the transducer, e.g. by a snap-in connection, not before implantation of the transducer. Then, if an exchange becomes necessary, this transducer-side coupling element is supplied as a separate exchangeable part together with a new transducer in a sterile packing.

Figure 10:
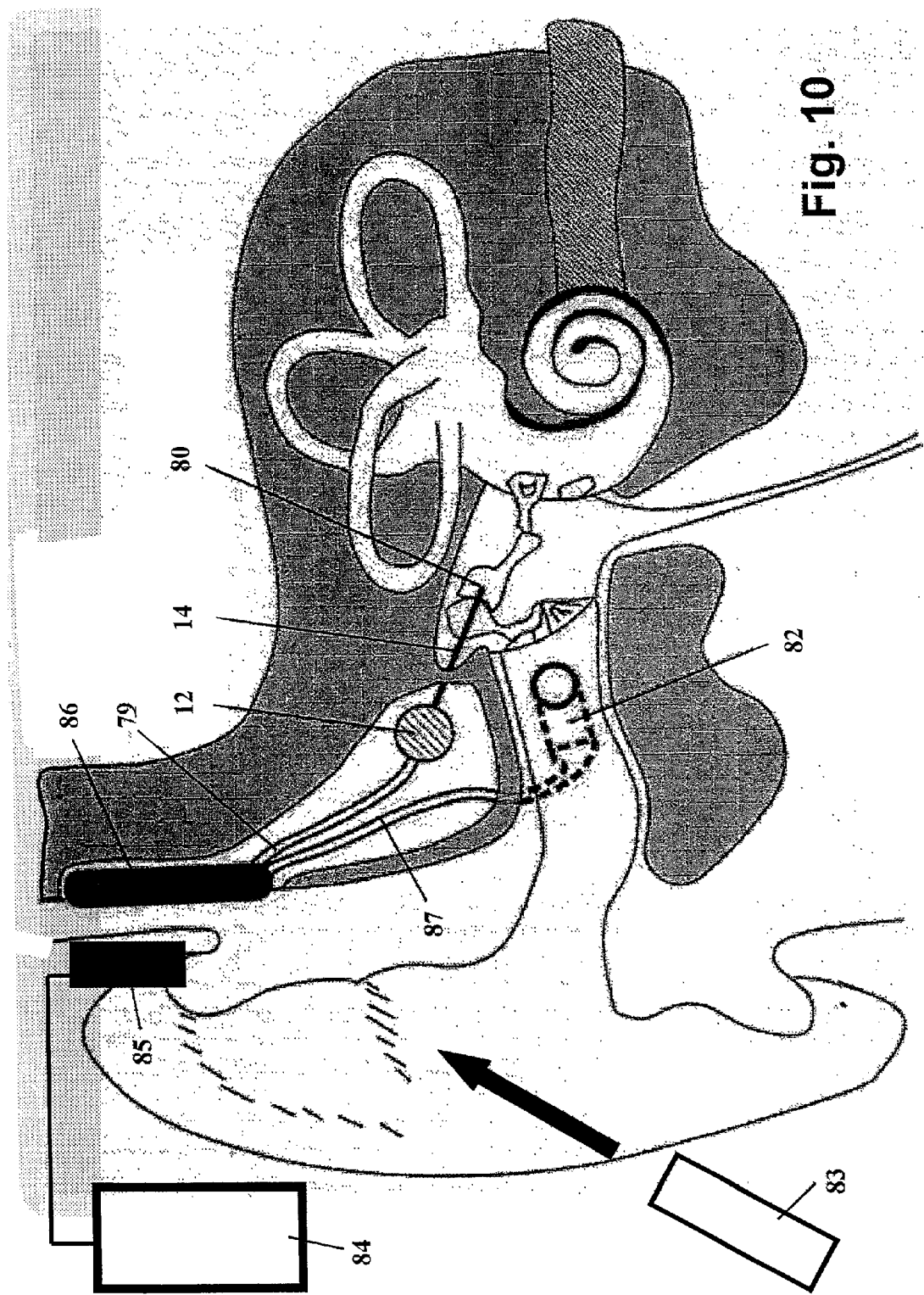
FIG. 10 shows an embodiment of a fully implantable hearing system.

FIG. 10 shows a fully implantable hearing system having as actoric stimulation means an electromechanical output transducer 12 which is releasably coupled to the micromanipulator 18 (which is not shown in FIG. 10 but particularly in FIG. 3) via a transducer-side coupling element 22 or 54 or 58, respectively. The transducer 12 generally may be any electromagnetic, electrodynamic, piezoelectric, magnetostrictive, or dielectric (capacitive) transducer. A preferred embodiment of a piezoelectric transducer is known from commonly owned U.S. Pat. No. 5,277,694 which is hereby incorporated by reference. Such a transducer is provided with a biocompatible cylindrical housing 78 (FIG. 3) of electrically conductive material, such as titanium. The housing 78 is filled with an inert gas. An electrically conductive membrane that can oscillate, is disposed within the housing 78. The membrane preferably is circular, and it is fixedly connected to housing 78 at the outer edge thereof A thin disk of piezoelectric material, e.g. lead-zirconate-titanate (PTZ), is provided at one side of the membrane. The side of the piezoelectric disk facing the membrane is in electrically conductive connection with the membrane. Application of an electrical voltage to the piezoelectric disk via a transducer line 79 results in a deformation of the hetero-compound consisting of the membrane and the piezoelectric disk, and thus in a deflection of the membrane and of the coupling rod 14 attached thereto. Such a transducer 12 typically has a relatively high mechanical output impedance, particularly a mechanical output impedance which is higher than the mechanical load impedance of the biological structure of the middle ear and/or the inner ear coupled to the transducer in the implanted state. The transducer 12, amongst others, may be modified in the manner explained in commonly owned U.S. Pat. No. 6,123,660, which is hereby incorporated by reference, such that a permanent magnet is attached at the side of the piezoelectric ceramic disk remote from the membrane, which permanent magnet cooperates with an electromagnetic coil in the manner of an electromagnetic transducer. Such a combined piezoelectric-electromagnetic transducer is of advantage particularly with respect to a broad frequency band and to attain relatively high oscillation amplitudes at relatively small amounts of supplied energy.

The transducer 12 further may be an electromagnetic transducer of the type described in commonly owned U.S. Pat. No. 6,162,169 which is hereby incorporated by reference.

To couple the electromechanical transducer 12 to the middle ear or the inner ear (for example to the incus at coupling site 80), especially coupling arrangements as described in commonly owned U.S. Pat. No. 5,941,814, which is hereby incorporated by reference, are suited in which a coupling element, in addition to a coupling part for the pertinent coupling site, has a crimp sleeve which is first slipped loosely onto a rod-shaped part of a coupling rod connected to the transducer in the above described manner. This rod-shaped part of the coupling rod is provided with a rough surface. During implantation, the crimp sleeve can simply be pushed and turned relative to the coupling rod to exactly align the coupling part of the coupling element with the intended coupling site. Then, the crimp sleeve is fixed by being plastically cold-deformed by means of a crimping tool. Alternatively, the coupling element can be fixed with reference to the coupling rod by means of a belt loop which can be tightened.

Other coupling arrangements which can be preferably used here are described, in particular, in commonly owned, co-pending U.S. patent applications Ser. Nos. 09/576,009, 09/626,745, 09/613,560, 09/680,489 and 09/680,488, all of which hereby are incorporated by reference. Thus, according to commonly owned, co-pending U.S. patent application Ser. No. 09/576,009, a coupling element can have a contact surface on its coupling end which has a surface shape which is matched to or can be matched to the surface shape of the coupling site, and has a surface composition and surface size such that, by placing the coupling end against the coupling site, dynamic tension-compression force coupling of the coupling element and ossicular chain occur due to surface adhesion Ser. which is sufficient for secure mutual connection of the coupling element and the ossicular chain. The coupling element can be provided with an attenuation element which adjoins the coupling site, in the implanted state, and which has entropy-elastic properties in order to achieve an optimum form of vibration of the footplate of the stapes or of the membrane which closes the round window or an artificial window in the cochlea, in the vestibulum or in the labyrinth, and especially to minimize the risk of damage to the natural structures in the area of the coupling site during and after implantation (see commonly owned, co-pending U.S. patent application Ser. No. 09/626,745).

According to commonly owned co-pending U.S. patent application Ser. No. 09/613,560 the coupling element can be provided with an actuation device for selectively moving the coupling element between an open position, in which the coupling element can engage and disengage the coupling site, and a closed positioning, in which the coupling element in the implanted state is connected by force-fit and/or form-fit to the coupling site.

Furthermore, for mechanically coupling the electromechanical transducer to a pre-selected coupling site on the ossicular chain, a coupling arrangement (see commonly owned, co-pending U.S. patent application Ser. No. 09/680, 489) is suitable which has a coupling rod which can be caused by the transducer to mechanically vibrate, and a coupling element which can be connected to the pre-selected coupling site. The coupling rod and the coupling element are interconnected by at least one coupling, and at least one section of the coupling element which, in the implanted state, adjoins the coupling site is designed for low-loss delivery of vibrations to the coupling site, the first half of the coupling having an outside contour with at least roughly the shape of a spherical dome which can be accommodated in the inside contour of a second coupling half that is at least partially complementary to the outside contour. The coupling has the capacity to swivel and/or turn reversibly against forces of friction, but is essentially rigid for the dynamic forces which occur in the implanted state. According to a modified embodiment of such a coupling arrangement (see commonly owned, co-pending U.S. patent application Ser. No. 09/680,488) the first half of the coupling has an outside contour with an at least cylindrical, preferably circularly cylindrical, shape which can be accommodated in the inside contour of a second coupling half that is at least partially complementary to the outside contour. A section of the coupling element, which adjoins the coupling site in the implanted state, is designed for low-loss delivery of vibrations to the coupling site in the implanted state, transmission of dynamic forces between the two halves of the coupling taking place essentially in the direction of the lengthwise axis of the first coupling half The coupling can be reversibly coupled and de-coupled, and can be reversibly moved linearly and/or rotationally with reference to the lengthwise axis of the first coupling half, but is rigid for the dynamic forces which occur in the implanted state.

The fully implantable hearing system shown in FIG. 10 further comprises an implantable microphone (sound sensor) 82, a wireless remote control 83 to control the implant functions by the implant wearer, and a charging system comprising a charger 84 and a charging coil 85 for wireless transcutaneous recharging of a secondary battery located in the implant for power supply of the hearing system.

The microphone 82 can advantageously be built in the manner known from commonly owned U.S. Pat. No. 5,814,095 which hereby is incorporated by reference. Particularly, microphone 82 can be provided with a microphone capsule which is accommodated hermetically sealed on all sides within a housing, and with an electrical feed-through connector for routing at least one electrical connection from within the housing to the outside thereof The housing has at least two legs which are arranged at an angle relative to one another, a first one of the legs containing the microphone capsule and being provided with a sound inlet membrane, and a second one of the legs containing the electrical feed-through connector and being set back relative to the plane of the sound inlet membrane. The geometry of the microphone housing is chosen such that when the microphone is implanted in the mastoid cavity the leg which contains the sound inlet membrane projects from the mastoid into an artificial hole in the posterior bony wall of the auditory canal and the sound inlet membrane touches the skin of the wall of the auditory canal. To fix the implanted microphone 82, there can preferably be a fixation element of the type known from commonly owned U.S. Pat. No. 5,999,632 which hereby is incorporated by reference. This fixation element has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging coil 85 connected to the output of the charging device 84 preferably forms part of the transmitting serial resonant circuit in the manner known from commonly owned U.S. Pat. No. 5,279,292 which hereby is incorporated by reference. The transmitting serial resonant circuit can be inductively coupled to a receiving serial resonant circuit which is not shown. The receiving serial resonant circuit can be part of the implantable electronic module 86, and according to U.S. Pat. No. 5,279,292, can form a constant current source for the battery. The receiving serial resonant circuit is connected in a battery charging circuit which, depending on the respective phase of the charging current flowing in the charging circuit, is closed via one branch or the other of a full wave rectifier bridge.

The electronic module 86 is connected in the arrangement as shown in FIG. 10 via a microphone line 87 to the microphone 82 and via the transducer line 79 to the electromechanical transducer 12

Figure 11:
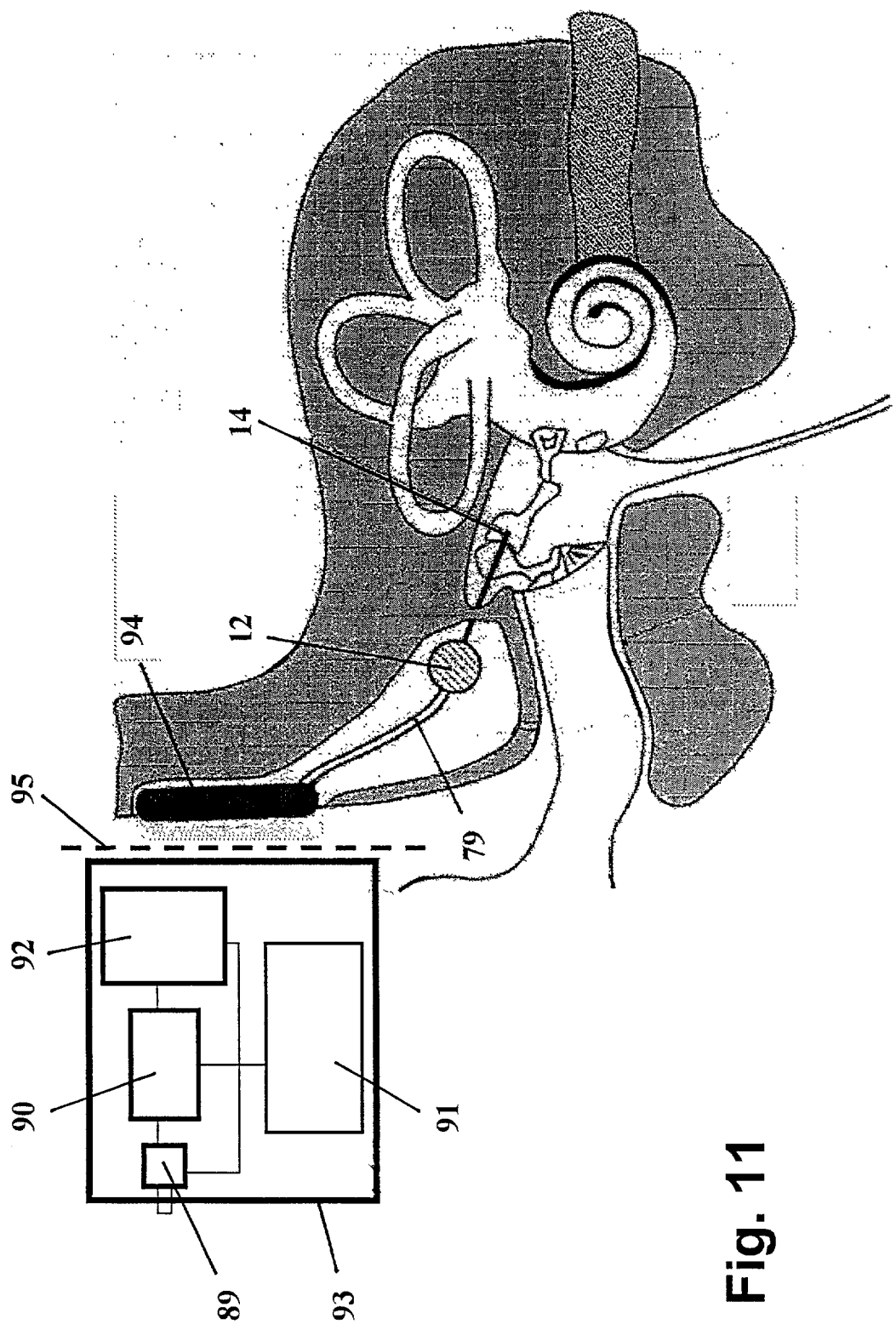
FIG. 11 shows an embodiment of a partially implantable hearing system.

FIG. 11 schematically shows the structure of a partially implantable hearing system. This partially implantable system includes a microphone 89, an electronic module 90 for electronic signal processing, the power supply (battery) 91 and a modulator/transmitter unit 92 in an external module 93 which is to be worn externally on the body, preferably on the head over the implant. As in known partial implants, the implant is passive in terms of energy. Its electronic module 94 (without battery) receives its operating energy and control signals for the transducer 12 via the modulator/transmitter unit 92 in the external module 93.

Both the fully implantable hearing system and the partially implantable hearing system may be designed as a monaural system (as illustrated in FIGS. 10 and 11) or as a binaural system. A binaural system for rehabilitation of a hearing disorder of both ears comprises a pair of system units, each of which units is associated to one of the two ears. Both system units may be essentially identical to one another. But one system unit can also be designed as a master unit and the other system unit as the slave unit which is controlled by the master unit. The signal processing modules of the two system units can communicate with one another in any way, especially via a wired implantable line connection or via a wireless connection, preferably a bidirectional high frequency path, a bodyborne sound-coupled ultrasonic path or a data transmission path which uses the electrical conductivity of the tissue of the implant wearer, such that in both system units optimized binaural signal processing is achieved.

Particularly, the following possibilities of combinations are possible:

Both electronic modules may each contain a digital signal processor, and the operating software of the two processors can be transcutaneously changed, if required. Then the connection of the two modules provides essentially for data exchange for optimized binaural signal processing, for example, of the sensor signals.

Only one module contains the digital signal processor. The module connection then provides, in addition to transmission of sensor data for binaural sound analysis and balancing, for transfer of the output signal to the contralateral transducer, wherein the latter module can house the electronic transducer driver. In this case, the operating software of the entire binaural system is filed in only one module, and the software also is changed transcutaneously only in this module from the outside via a telemetry unit which is present on only one side. In this case, the power supply of the entire binaural system can be housed in only one electronic module with power being supplied by wire or wirelessly to the contralateral module.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

We claim:

1. A method of implanting an at least partially implantable hearing system comprising:
   fixedly attaching a micromanipulator to the cranial vault of a recipient, said micromanipulator having a manipulator-side coupling attached thereto;
   positioning said micromanipulator in a desired position;
   fixedly connecting a transducer-side coupling element to an electromechanical transducer in the course of an implantation of said transducer;
   releasably coupling said micromanipulator to said transducer, comprising:
      snapping said transducer-side coupling element into said micromanipulator-side coupling element to mechanically lock said transducer-side coupling element therein.

2. The method of claim 1, further comprising:
   decoupling said transducer-side coupling element from said micromanipulator-side coupling element, and
   removing said transducer from said recipient.

3. The method of claim 2, further comprising:
   coupling a replacement transducer, having a transducer-side coupling element, to said micromanipulator.

4. An at least partially implantable hearing system comprising:
   at least one electromechanical output transducer;
   a micromanipulator configured to be fixedly attached to a recipient's cranial vault and, once so attached, to rotationally and axially position, and fixedly retain, said at least one transducer; and
   a coupling unit, disposed between said transducer and said micromanipulator, configured to permit decoupling of said transducer from said micromanipulator while maintaining the position of said micromanipulator, comprising:
      a transducer-side coupling element, connected to said transducer, having a first configuration and an at least partially deformed second configuration,
      a micromanipulator-side coupling element connected to said micromanipulator configured to receive said transducer-side element, and
      wherein said transducer-side coupling element adopts said second configuration during insertion into said micromanipulator-side element, and regains said first configuration following insertion, to thereby mechanically lock said transducer-side coupling element into said micromanipulator-side coupling element.

5. The device of claim 4, wherein said transducer-side coupling element is configured to be axially pressed into said micromanipulator-side coupling element.

6. The device of claim 4, wherein said transducer-side coupling element is made of a resiliently flexible material.

7. The device of claim 4, wherein said micromanipulator-side coupling element is a rigid annular receiver member.

8. The device of claim 4, wherein said transducer-side coupling element is configured to decouple from micromanipulator-side coupling element when said head is compressed at least slightly.

9. The device of claim 4, wherein said transducer-side coupling element comprises:
   a truncated head having an at least partially circular base;
   a cylindrical neck, connected to and aligned with said base along an axis through the center of said base, extending longitudinally away from said base, and having a circumference that is smaller than that of said base, and
   a collar extending radially from said neck at an end of said neck remote from said base.

10. The device of claim 9, wherein said micromanipulator-side coupling element comprises:
    a circular cylindrical receiver having an inner diameter is approximately the same as the outer of said neck, and an outer diameter that is smaller than a diameter of said base.

11. The device of claim 4, wherein said transducer-side coupling element is at least partially made of elastic material.

12. The system of claim 11, wherein said elastic material is a polymeric material.

* * * * *